United States Patent [19]

Takeuchi et al.

[11] Patent Number: 5,762,992
[45] Date of Patent: Jun. 9, 1998

[54] METHOD OF PREVENTING A DECREASE IN SWEETNESS OF THAUMATIN

[75] Inventors: Masanori Takeuchi, Nishinomiya; Takashi Onishi, Osaka; Hiroki Iida, Nishikyo-ku; Kazushi Sakaue, Mitaka; Takashi Ochi, Kobe; Shiro Ohashi, Sakai, all of Japan

[73] Assignee: San-EI Chemical Industries, Ltd., Osaka, Japan

[21] Appl. No.: 919,267

[22] Filed: Jul. 27, 1992

[30] Foreign Application Priority Data

Aug. 1, 1991 [JP] Japan ................................. 3-193259

[51] Int. Cl.$^6$ ............................................. A23L 1/236
[52] U.S. Cl. ........................................ 426/548; 426/658
[58] Field of Search ........................... 426/548, 658

[56] References Cited

FOREIGN PATENT DOCUMENTS

| | | |
|---|---|---|
| 62-83877 | 4/1987 | Japan . |
| 63-63388 | 3/1988 | Japan . |
| 1128775 | 5/1989 | Japan . |
| 1291799 | 11/1989 | Japan . |
| 2174649 | 7/1990 | Japan . |
| 2231065 | 9/1990 | Japan . |
| 2123672 | 2/1984 | United Kingdom . |

OTHER PUBLICATIONS

Dialog Data Base, File 5 (Biosis Previews), Dialog Acc. #8633968, Abstracting Food Hydrocolloids 5 (4), 1991, 375–392.

Dialog Data Base, File 351, (Derwent World Patent Index), Dialog Acc No. 008363662, Abstracting JP2174649.

Shiro OHASHI et al., "Interaction of thaumatin with carrageenans. IV. Method for prevention of reduction of sweetness intensity of thaumatin in interaction with carrageenan at ph 4", *Food Hydrocolloids*, vol. 5, No. 4, pp. 375–391, (1991), which corresponds to Reference R on PTO form 892.

*Primary Examiner*—Leslie Wong
*Attorney, Agent, or Firm*—Greenblum & Bernstein P.L.C.

[57] ABSTRACT

A method of preventing a decrease in sweetness of thamatin, characterized in that, chitosan or hydrolyzed chitosan is added to thaumatin in an amount which is effective for prevention of a decrease in sweetness of thaumatin.

11 Claims, No Drawings

5,762,992

METHOD OF PREVENTING A DECREASE IN SWEETNESS OF THAUMATIN

BACKGROUND OF THE INVENTION

1. Field of the Invention

The present invention relates to a method of preventing a decrease in sweetness of thaumatin.

2. Description of the Prior Art

Thaumatin is a sweetening agent obtained by extraction from aril of fruit of a plant Thaumatococcus Danielli Benth. or by recombination of gene of microorganism.

The present inventors have formerly found that, when negatively-charged substance (e.g. fruit juice and anionic surface active agent) is present in aqueous solution of thaumatin, precipitates are formed and that it is effective to use chitosan for preventing such precipitation and also to use ascorbic acid and chitosan together for preventing unpleasant after-taste of aqueous solution of thaumatin (cf. Japanese Laid-Open Publication 02/174,649).

On the other hand, sweetness of thaumatin decreases when an aqueous solution of thaumatin contains coloring agents such as Tartrazine, Sunset Yellow, Ponceau 4R, lac dyes and cochineal dyes of the anthraquinone series; red cabbage dyes of anthocyanin series; annatto dyes of the carotenoid series; or safflower yellow dyes of the flavonoid series) or polysaccharides (such as carrageenan, xanthan gum, sodium carboxymethylcellulose, sodium alginate, high methoxyl pectin, locust bean gum or guar gum). However, no method for preventing it has been found yet.

SUMMARY OF THE INVENTION

The present invention relates to a method of preventing a decrease in sweetnesss of thaumatin in the presence of additives which are commonly used for foods, drugs, drug-related substances etc. such as coloring agents and polysaccharides.

The present invention provides a method of preventing a decrease in sweetness of thaumatin, characterized in that, chitosan or hydrolyzed chitosan (in an amount which is effective for preventing the decrease in the sweetness of thaumatin) is added to thaumatin.

PREFERRED EMBODIMENT OF THE INVENTION

Chitosan used in the present invention is a substance obtained by deacetylation of chitin (contained in shell etc. of Crustaceae such as crab and shrimp) with alkali.

Hydrolized chitosan is a substance obtained by hydrolysis of chitosan with an acid or enzyme. More specifically, in hydrolyzing, for example, with acid, there is a method of hydrolyzing by the use of an inorganic acid such as hydrochloric acid or organic acid such as acetic acid at the temperature of 100°–121° C. for 5 to 180 minutes as disclosed in Japanese Laid Open Publication 01(1989)/128775. With respect to hydrolysis with enzymes, there are methods of hydrolyzing by the use of enzyme such as acidic protease, pectinase, cellulase, papain, chitosanase, at pH 3–5 and 40°–60° C. for 1–24 hours as disclosed, for example, in Japanese Laid Open Publications 62/83877 and 63/63388, Japanese Patent Application 121852/88 and Japanese Laid Open Publication 02/231,065. Depending upon the average molecular weight of the chitosan to be prepared, the temperature and the time may be adjusted.

It has been found that the average molecular weight (calculated from the calibration curve prepared by means of gel permeation chromatography using dextran as a standard substance) of the hydrolyzed chitosan used in the present invention is to be preferably within a range of about 2,000 to 100,000. When the average molecular weight is less than 2,000, there is no effect of prevention of a decrease in sweetness of thaumatin while, when it is more than 100,000, astringent taste is resulted. Incidentally, hydrolyzed chitosans with varied molecular weights may be mixed and used.

With regard to the effective amount for preventing a decrease in sweetness of thaumatin, there are some differences between chitosan and hydrolyzed chitosan. The amount of hydrolyzed chitosan to 1 part by weight of thaumatin is 0.0002–100 parts by weight or, preferably, 0.0025–10 parts by weight though the amount is correspondent to the molecular weight of hydrolyzed chitosan. Thus, when the molecular weight is small, the amount may be much and, even if used in large amount, no astringent taste is resulted. On the other hand, the amount of chitosan to 1 part by weight of thaumatin is 0.0002–100 parts by weight or, perferably, 0.0025–1 part by weight.

It is also possible to use chitosan and hydrolyzed chitosan jointly. When the method of the present invention is carried out in an aqueous solution of pH 6 or higher, it is preferred to use hydrolyzed chitosan from a viewpoint of solubility etc.

The method of the present invention is usually conducted in a state of aqueous solution in which thaumatin is present together with other additives. Methods for preparing the solution will be that (i) chitosan or hydrolyzed chitosan is made into an acidic aqueous solution and thaumatin is added thereto; (ii) chitosan or hydrolyzed chitosan is dissolved in (acidic) aqueous solution of thaumatin followed by adding other additives thereto; or (i) or (ii) is added to aqueous solution of the additives whereupon desired liquidal preparation is abstained. In the case of solid preparation, a solution containing certain amounts of thaumatin and chitosan or hydrolyzed chitosan is spray-dried or lyophilized and the resulting powder is used.

The method of the present invention is applicable in any of the fields including foods, drugs, cosmetics, feeds etc. in which thaumatin is used as a sweetening agent.

The effect of the present invention is illustrated by way of the following test examples.

TEST EXAMPLE 1.

Preparation of the Sample Solution.

Adjustment of each of the following sample solutions to pH 4 or pH 6 was conducted by 0.01N or 0.1N hydrochloric acid or sodium hydroxide.

a: Thaumatin solution (0.04% w/v) adjusted to pH 4 or pH 6 was prepared and kept at 40° C.

b: Chitosan of average molecular weight of about $1.19 \times 10^6$ (hereinafter, referred to as "chitosan A") was dissolved in 0.08% (w/v) of acetic acid solution so as to make the concentration of chitosan A 0.04% (w/v). Hydrolyzed chitosan of average molecular weight of about $5.6 \times 10^4$ (hereinafter, referred to as "hydrolyzed chitosan B") was dissolved in 8% (w/v) acetic acid solution so as to make the concentration of hydrolyzed chitosan B 4% (w/v).

The chitosan A solution of 0.04% (w/v) was adjusted to pH 4 or 6 followed by diluting with water (adjusted to pH 4 or 6) to prepare chitosan A solutions of $4 \times 10^{31\ 8}$, $4 \times 10^{-7}$, $4 \times 10^{-6}$, $8 \times 10^{-6}$, $4 \times 10^{-5}$, $1 \times 10^{-4}$, $2 \times 10^{-4}$, $4 \times 10^{-4}$, $8 \times 10^{-4}$, $8 \times 10^{-3}$ and 0.04% (w/v) concentrations. Those solutions were kept at 40° C.

The hydrolyzed chitosan B solution of 4% (w/v) was similarly adjusted to pH 4 or 6 followed by diluting with water which was adjusted to pH 4 or 6 to prepare hydrolyzed chitosan B solutions of 0.04, 0.4, 0.8, 2.0 and 4% (w/v). The solutions were kept at 40° C. Aqueous solutions of chitosan A of 0.4% (w/v) and higher concentrations were very highly viscous whereby their mixing with thaumatin solution was difficult. Accordingly, hydrolyzed chitosan B with low viscosity was used.

c: lamda-Carrageenan solution of 0.08% (w/v) adjusted to pH 4 or that of 0.45% (w/v) adjusted to pH 6 was prepared and kept at 40° C. The amount of the lamda-carrageenan was chosen in such a manner that the sweet taste of thaumatin of final concentration of 0.01% (w/v) at pH 4 and 6 completely disappeared.

II: Mixing the Sample Solutions.

Each of the sample solutions which were adjusted to pH 4 or 6 and kept at 40° C. was mixed in accordance with the following procedures.

II-1: Effect of the order mixing three sample solutions on the sweet taste of thaumatin.

a: To 50 ml of thaumatin solution was added 50 ml of 0.04% (w/v) chitosan A solution followed by mixing for one minute. Then 100 ml of lamda-carrageenan solution was added and the mixture was shaken at 40° C. for 5 minutes.

b: To 50 ml of Thaumatin solution was added 100 ml of lamda-carrageenan solution followed by mixing for one minute. Then 50 ml of 0.04% (w/v) chitosan A solution was added and the-mixture was shaken at 40° C. for 5 minutes.

c: To 50 ml of 0.04% (w/v) chitosan A solution was added 100 ml of lamda-carrageenan solution followed by mixing for one minute. Then 50 ml of thaumatin solution was added and the mixture was shaken at 40° C. for 5 minutes.

The mixed solutions of a, b and c were heated at 80° C. (liquid temperature) for 10 minutes and cooled down to 25° C. in cold water of 10° C.

II-2: Effect of the concentrations of chitosan A or hydrolyzed chitosan B solution (wherein the mixing order of the three sample solutions were same) on the sweetness of thaumatin.

Mixing method was the same as that in the above II-1 a. Thus, to 50 ml of thaumatin solution was added each 50 ml of chitosan A or hydrolyzed chitosan B solution of various concentrations followed by mixing for one minute. Then 100 ml of lamda-carrageenan solution was added and the mixture was shaken at 40° C. for 5 minutes.

The mixed solutions prepared in accordance with the above II-1 and II-2 were heated at 80° C. (liquid temperature), for 10 minutes and cooled down to 25° C. in cold water of 10° C.

Control solution was prepared as follows. Thus, 50 ml of thaumatin solution, 100 ml of lamda-carrageenan solution and 50 ml of water (which was adjusted to pH 4 or 6 and kept at 40° C.) were mixed, the mixture was shaken at 40° C. for 5 minutes, heated at 80° C. (liquid temperature) for 10 minutes and cooled down to 25° C. in cold water of 10° C.

III. Organoleptic Test of Sweetness of Thaumatin.

a: Preparation of standard sweet solution.

Standard sweet solutions of thaumatin (pH being adjust to 4 or 6) of 0 to 0.01% (w/v) with a concentration interval of 0.001% (w/v) were prepared.

b:organoleptic method.

Sweetness of 0.01, 0.009, 0.008, . . . , 0.001 and 0% (w/v) thaumatin solution was defined to be 100, 90, 80, . . . , 10 and 0, respectively.

Panellers comprised of each ten males and females. Instruction was given to the panellers that they should choose a standard sweetness solution having the same sweetness as that of each one of mixed sample solutions of pH 4 and 6. The results were collected, subjected to a verification by a pair test and the sweetness which was significant at $p<0.05$ was judged to be the sweetness of the mixed sample solution.

TABLE 1

Effect of the Mixing Order of the Sample Solutions on the Sweetness of Thaumatin Sweetness of Thaumatin (%)

| | Final Concn of Chitosan A % (w/v) | Final Concn of Thaumatin % (w/v) | Final Concn of λ-Carrageenan % (w/v) at | | pH 4 Heating Temperature(°C.) | | pH 6 Heating Temperature(°C.) | |
|---|---|---|---|---|---|---|---|---|
| | | | pH 4 | pH 6 | 40 | 80 | 40 | 80 |
| Control Soln | — | 0.01 | 0.04 | 0.225 | 0 | 0 | 0 | 0 |
| Sample Soln a | 0.01 | 0.01 | 0.04 | 0.225 | 100 | 90 | 100 | 100 |
| Sample Soln b | 0.01 | 0.01 | 0.04 | 0.225 | 30 | 30 | 80 | 80 |
| Sample Soln c | 0.01 | 0.01 | 0.04 | 0.225 | 30 | 30 | 90 | 90 |

Sample Soln a: Thaumatin → Chitosan A → lamda-Carrageenan
Sample Soln b: Thaumatin → lamda-Carrageenan → Chitosan A
Sample Soln c: Chitosan A → lamda-Carrageenan → Thaumatin

TABLE 2

Effect of Concentrations of Solutions of A or B
(of Sample Solution a with the Same Mixing Order)
on Sweetness of Thaumatin

| Type of Chitosan | Concn Ratio of A or B to Thaumatin (w/w) | Final Concn of A or B % (w/v) | Final Concn of Thaumatin % (w/v) | Final Concn of λ-Carrageenan % (w/v) at pH 4 | Final Concn of λ-Carrageenan % (w/v) at pH 6 | Sweetness of Thaumatin (%) pH 4 heated at 40 | Sweetness of Thaumatin (%) pH 4 heated at 80 | Sweetness of Thaumatin (%) pH 6 heated at 40 | Sweetness of Thaumatin (%) pH 6 heated at 80° C. |
|---|---|---|---|---|---|---|---|---|---|
| Control Soln | 0:1 | 0 | 0.01 | 0.04 | 0.225 | 0 | 0 | 0 | 0 |
| A | 0.000001:1 | $1 \times 10^{-3}$ | 0.01 | 0.04 | 0.225 | 0 | 0 | 0 | 0 |
|   | 0.00001:1 | $1 \times 10^{-7}$ | 0.01 | 0.04 | 0.225 | 0 | 0 | 0 | 0 |
|   | 0.0001:1 | $1 \times 10^{-4}$ | 0.01 | 0.04 | 0.225 | 0 | 0 | 0 | 0 |
|   | 0.0002:1 | $2 \times 10^{-5}$ | 0.01 | 0.04 | 0.225 | 20 | 20 | 30 | 40 |
|   | 0.001:1 | $1 \times 10^{-6}$ | 0.01 | 0.04 | 0.225 | 40 | 30 | 50 | 60 |
|   | 0.0025:1 | $0.25 \times 10^{-4}$ | 0.01 | 0.04 | 0.225 | 80 | 70 | 90 | 100 |
|   | 0.005:1 | $0.5 \times 10^{-4}$ | 0.01 | 0.04 | 0.225 | 60 | 50 | 100 | 100 |
|   | 0.01:1 | $1 \times 10^{-4}$ | 0.01 | 0.04 | 0.225 | 60 | 50 | 100 | 100 |
|   | 0.02:1 | $2 \times 10^{-4}$ | 0.01 | 0.04 | 0.225 | 60 | 50 | 100 | 90 |
|   | 0.1:1 | $1 \times 10^{-3}$ | 0.01 | 0.04 | 0.225 | 80 | 70 | 100 | 100 |
|   | 1:1 | 0.01 | 0.01 | 0.04 | 0.225 | 100 | 90 | 100 | 100 |
| B | 1:1 | 0.01 | 0.01 | 0.04 | 0.225 | 90 | 80 | 100 | 90 |
|   | 10:1 | 0.1 | 0.01 | 0.04 | 0.225 | 80 | 70 | 80 | 70 |
|   | 20:1 | 0.2 | 0.01 | 0.04 | 0.225 | 50 | 40 | 50 | 40 |
|   | 50:1 | 0.5 | 0.01 | 0.04 | 0.225 | 30 | 30 | 30 | 40 |
|   | 100:1 | 1.0 | 0.01 | 0.04 | 0.225 | 20 | 20 | 30 | 40 |

Note:
A - Chitosan A
B - Hydrolyzed Chitosan B

TEST EXAMPLE 2.

I: Preparation of the Sample Solution a: Thaumatin solution (the same as that in Test Example 1)

b: Chitosan or hydrolyzed chitosan solution.

Hydrolyzed chitosan of average molecular weight of about $1\times10^4$ (hereinafter, referred to as "hydrolyzed chitosan C"), hydrolyzed chitosan of average molecular weight of about $3.92\times10^3$ ("chitosan D"), hydrolyzed chitosan of average molecular weight of about $1\times10^3$ ("chitosan E") and chitosan A and hydrolyzed chitosan B used in Test Example 1 were used. Solutions adjusted to pH 4 or 6 containing $4\times10^{-3}$, 0.04 and 0.4% (w/v) of chitosan or hydrolyzed chitosan were prepared.

c: lamda-Carrageenan solution (the same as that in Test Eample 1)

2: Mixing of the sample solutions (the same as a method II-a of Test Example 1).

3: Organoleptic test of sweetness of thaumatin (the same as that in TEST example 1).

TABLE 3

Effect of Degree of Decomposition of Chitosan on Sweetness of Thaumatin

| | Ratio of Concn of A, B, C, D or E to Thaumatin (w/w) | Final Concn of A, B, C, D, or E % (w/v) | Final Concn of Thaumatin % (w/v) | Final Concn of λ-Carrageenan % (w/v) at pH 4 | Final Concn of λ-Carrageenan % (w/v) at pH 6 | Sweetness of Thaumatin (%) at pH 4 heated at 40° C. | Sweetness of Thaumatin (%) at pH 4 heated at 80° C. | Sweetness of Thaumatin (%) at pH 6 heated at 40° C. | Sweetness of Thaumatin (%) at pH 6 heated at 80° C. |
|---|---|---|---|---|---|---|---|---|---|
| Control Soln | 0:1 | 0 | 0.01 | 0.04 | 0.225 | 0 | 0 | 0 | 0 |
| A | 0.1:1 | $1 \times 10^{-3}$ | 0.01 | 0.04 | 0.225 | 80 | 70 | 100 | 100 |
|   | 1:1 | 0.01 | 0.01 | 0.04 | 0.225 | 100 | 90 | 100 | 100 |
| A and B (1:1) | 10:1 | 0.1 | 0.01 | 0.04 | 0.225 | 90 | 80 | 100 | 100 |
| B | 0.1:1 | $1 \times 10^{-3}$ | 0.01 | 0.04 | 0.225 | 80 | 70 | 90 | 90 |
|   | 1:1 | 0.01 | 0.01 | 0.04 | 0.225 | 90 | 80 | 100 | 90 |
|   | 10:1 | 0.1 | 0.01 | 0.04 | 0.225 | 80 | 70 | 80 | 70 |

TABLE 3-continued

Effect of Degree of Decomposition of Chitosan on Sweetness of Thaumatin

| | Ratio of Concn of A, B, C, D or E to Thaumatin (w/w) | Final Concn of A, B, C, D, or E % (w/v) | Final Concn of Thaumatin % (w/v) | Final Concn of λ-Carrageenan % (w/v) at pH 4 | pH 6 | Sweetness of Thaumatin (%) at pH 4 heated at 40° C. | 80° C. | pH 6 heated at 40° C. | 80° C. |
|---|---|---|---|---|---|---|---|---|---|
| C | 0.1:1 | $1 \times 10^{-3}$ | 0.01 | 0.04 | 0.225 | 70 | 60 | 80 | 70 |
|   | 1:1   | 0.01 | 0.01 | 0.04 | 0.225 | 80 | 70 | 90 | 80 |
|   | 10:1  | 0.1  | 0.01 | 0.04 | 0.225 | 70 | 60 | 80 | 70 |
| D | 0.1:1 | $1 \times 10^{-3}$ | 0.01 | 0.04 | 0.225 | 40 | 40 | 70 | 70 |
|   | 1:1   | 0.01 | 0.01 | 0.04 | 0.225 | 40 | 40 | 70 | 70 |
|   | 10:1  | 0.1  | 0.01 | 0.04 | 0.225 | 30 | 30 | 60 | 60 |
| E | 0.1:1 | $1 \times 10^{-3}$ | 0.01 | 0.04 | 0.225 | 0 | 0 | 0 | 0 |
|   | 1:1   | 0.01 | 0.01 | 0.04 | 0.225 | 0 | 0 | 0 | 0 |
|   | 10:1  | 0.1  | 0.01 | 0.04 | 0.225 | 0 | 0 | 0 | 0 |

Notes:
A - Chitosan A
B - Hydrolyzed chitosan B
C - Hydrolyzed chitosan C
D - Hydrolyzed chitosan D
E - Hydrolyzed chitosan E

TEST EXAMPLE 3.

I: Preparation of Sample Solutions.

a: Thaumatin solution:(the same as that in Test Example 1).

b: Chitosan solution:

Solution adjusted pH 4 or 6 containing $4 \times 10^{-4}$ and 0.04% (w/v) of chitosan A were prepared.

c: Solutions of coloring agent or polysaccharide: Solutions (adjusted to pH 4 or 6) containing 0.4% (w/v) of xanthan gum, carboxymetbylcellulose sodium, sodium alginate or high methoxyl pectin; that containing 0.01% (w/v) of Tartrazine pigment; and those containing 0.4% (w/v) of lac dye, cochineal dye, red cabbage dye, annatto dye and safflower dye were prepared and kept at 40° C.

II: Mixing of the Sample Solutions.

Each of the sample solutions adjusted to pH 4 or 5 and kept at 40° C. was mixed in accordance with the following procedures.

To 50 ml of thaumatin solution was added 50 ml each of chitosan A solution of varied concentrations followed by mixing for one minute.

Then 100 ml of polysaccharide solution or coloring agent solution was added and the mixture was shaken for 5 minutes, heated at 80° C. (liquid temperature) for 10 minutes and cooled down to 25° C. in cold water of 10° C.

Control solutions were prepared as follows. Thus, 50 ml of thaumatin solution, 100 ml of solution of coloring agent or polysaccaride and 50 ml of water (which was adjusted to pH 4 or 6 and kept at 40° C.) were mixed and mixture was shaken at 40° C. for 5 minutes heated at 80° C. (liquid temperature) for 10 minutes and cooled down to 25° C. in cold water of 10° C.

3: Organoleptic test of sweetness of thaumatin was conducted by the same manner as in Test Example 1.

TABLE 4

Effect of Polysaccharides and Coloring Agents on Sweetness of Thaumatin

| | Sweetness of Thaumatin (%) | | | | | | | | | | | |
|---|---|---|---|---|---|---|---|---|---|---|---|---|
| | pH = 4 | | | | | | pH = 6 | | | | | |
| Ratio of Chitosan A to (w/w) | 0:1 | | 0.01:1 | | 1:1 | | 0:1 | | 0.01:1 | | 1:1 | |
| Thaumatin Concns heated at | 40 | 80 | 40 | 80 | 40 | 80 | 40 | 80 | 40 | 80 | 40 | 80° C. |
| (Polysaccharides) | | | | | | | | | | | | |
| Xanthan gum | 0 | 0 | 70 | 60 | 100 | 100 | 10 | 0 | 90 | 100 | 100 | 100 |
| CMC-Na | 0 | 0 | 60 | 50 | 100 | 90 | 10 | 0 | 70 | 80 | 100 | 100 |
| Na alginate | 10 | 0 | 90 | 80 | 100 | 100 | 20 | 10 | 100 | 100 | 100 | 100 |
| High methoxylpectin | 0 | 0 | 60 | 50 | 100 | 90 | 10 | 0 | 70 | 80 | 100 | 90 |

TABLE 4-continued

Effect of Polysaccharides and Coloring Agents on Sweetness of Thaumatin

| | Sweetness of Thaumatin (%) | | | | | | | | | | | |
|---|---|---|---|---|---|---|---|---|---|---|---|---|
| | pH = 4 | | | | | | pH = 6 | | | | | |
| Ratio of Chitosan A to (w/w) | 0:1 | | 0.01:1 | | 1:1 | | 0:1 | | 0.01:1 | | 1:1 | |
| Thaumatin Concns heated at | 40 | 80 | 40 | 80 | 40 | 80 | 40 | 80 | 40 | 80 | 40 | 80° C. |
| (Coloring agents) | | | | | | | | | | | | |
| Tartrazine | 30 | 20 | 80 | 70 | 100 | 90 | 20 | 10 | 80 | 70 | 100 | 90 |
| Cochineal dye | 50 | 50 | 70 | 70 | 90 | 80 | 40 | 40 | 90 | 90 | 90 | 90 |
| Lac dye | 10 | 0 | 70 | 60 | 90 | 80 | 10 | 0 | 70 | 70 | 90 | 80 |
| Red cabbage dye | 30 | 30 | 90 | 100 | 80 | 80 | 20 | 10 | 70 | 70 | 80 | 100 |
| Annatto dye | 10 | 10 | 50 | 60 | 80 | 70 | 10 | 10 | 30 | 40 | 40 | 50 |
| Safflower dye | 50 | 60 | 80 | 90 | 70 | 80 | 30 | 20 | 70 | 80 | 40 | 50 |

(Notes) Final concentrations of the samples:
Thaumatin: 0.01% (w/v)
Chitosan A: 0.2% (w/v)
Polysaccharide: 0.2% (w/v)
Tartrazine: 0.01% (w/v)
Cochineal dye; lac dye; red cabbage dye; annatto dye; and safflowerdye: 0.2% (w/v) each

TEST EXAMPLE 4.

I: Preparation of Sample Solutions a: Thaumatin solution (the same as that in Test Example 1 with as exception that the solution was allowed to stand at room temperature)

b: Solution of chitosan or hydrolyzed chitosan:

A solution adjusted to pH 4 or 6 containing 0.04% (w/v) of chitosan A or hydrolyzed chitosan C and a 1:1 (by weight) mixture of chitosan A and hydrolyzed chitosan C were prepared and each of them was allowed to stand at room temperature.

c: lamda-Carrageenan solution: (the same as that in Test Example 1 with an exception that the solution was allowed to stand at room temperature)

II: Methods of Mixing and Drying of the Sample Solutions.

Each of the sample solutions which were adjusted at pH 4 or 6 and allowed to stand at room temperature was mixed in accordance with the following procedures.

To 500 ml of thaumatin solution was added 500 ml of chitosan or/and hydrolyzed chitosan solution followed by mixing for 2 minutes.

II-1: lamda-Carrageenan solution (100 ml) was added to 100 ml of mixed solution of thaumatin and chitosan or/and hydrolyzed chitosan and the mixture was shaken at 40° C. for 5 minutes, heated at 80° C. (liquid temperature) for 10 minutes and cooled down to 25° C. in cold water of 10° C.

II-2: A mixed solution (1,000 ml) of thaumatin and chitosan was:

(i) spray-dried using an atomizer of inlet temperature of 160° C., outlet temperature of 80° C. and revolution of 25,000 rpm; or (ii) lyophilized in vacuo (0.15 Torr) at −50° C. for 48 hours.

The resulting dried product (0.04 g) was mixed with water and dissolved at room temperature to make whole volume 100 ml. To this was added 100 ml of lamda-carrageenan solution and the mixture was shaken at 40° C. for 5 minutes heated at 80° C. (liquid temperature) for 10 minutes and cooled down to 25° C. in cold a water of 10° C.

III: Organoleptic Test of the Sweetness of Thaumatin was conducted by the same manner as in Test Example 1.

TABLE 5

Effect of Drying Method for the Mixed Solution of Thaumatin/Chitosan and/or Hydrolyzed Chitosan on Sweetness of Thaumatin

| | | | | | Sweetness of Thaumatin (%) | | | | |
|---|---|---|---|---|---|---|---|---|---|
| Form of Mixt of Thauma- tin/Chi- tosan and(or) Hydrol. Chitosan | Final Concn of Chi- tosan A % (w/v) | Final Concn of Hydro- lyzed Chito- san C % (w/v) | Final Concn of Thau- ma- tin % (w/v) | Final Concn of lamda- Carrageenan % (w/v) at | | pH 4 heated at | | pH 6 heated at | |
| | | | | pH 4 | pH 6 | 40 | 80 | 40 | 80° C. |
| Control Soln | — | — | 0.01 | 0.04 | 0.225 | 0 | 0 | 0 | 0 |
| Mixed | 0.01 | — | 0.01 | 0.04 | 0.225 | 100 | 90 | 100 | 100 |

TABLE 5-continued

Effect of Drying Method for the Mixed Solution of Thaumatin/Chitosan and/or Hydrolyzed Chitosan on Sweetness of Thaumatin Sweetness of Thaumatin (%)

| Form of Mixt of Thaumatin/Chitosan and(or) Hydrol. | Final Concn of Chitosan A % (w/v) | Final Concn of Hydrolyzed Chitosan C % (w/v) | Final Concn of Thaumatin % (w/v) | Final Concn of lamda-Carrageenan % (w/v) at pH 4 | Final Concn of lamda-Carrageenan % (w/v) at pH 6 | pH 4 heated at 40 | pH 4 heated at 80 | pH 6 heated at 40 | pH 6 heated at 80° C. |
|---|---|---|---|---|---|---|---|---|---|
| Chitosan Soln | 0.005 | 0.005 | 0.01 | 0.04 | 0.225 | 90 | 80 | 100 | 90 |
|  | — | 0.01 | 0.01 | 0.04 | 0.225 | 80 | 70 | 90 | 80 |
| Spray-dried Prod. | 0.01 | — | 0.01 | 0.04 | 0.225 | 100 | 100 | 100 | 100 |
|  | 0.005 | 0.005 | 0.01 | 0.04 | 0.225 | 100 | 90 | 100 | 100 |
|  | — | 0.01 | 0.01 | 0.04 | 0.225 | 90 | 80 | 100 | 90 |
| Lyophilized Prod. | 0.01 | — | 0.01 | 0.04 | 0.225 | 100 | 90 | 100 | 100 |
|  | 0.005 | 0.005 | 0.01 | 0.04 | 0.225 | 90 | 80 | 100 | 90 |
|  | — | 0.01 | 0.01 | 0.04 | 0.225 | 80 | 70 | 90 | 80 |

(EXAMPLES)

Example 1.

To 97 parts of water was added 1 part of glacial acetic acid and, after mixing, 1 part of chitosan A was added thereto and the mixture was stirred/dissolved at room temperature.

Thaumatin (1 part) was added to the solution and dissolved by the same manner. The resulting solution was spray-dried at the inlet and outlet temperatures of 160° C. and 80° C., respectively (hereinafter, the spray-dried product will be referred to as "dried thaumatin-chitosan").

Dried thaumatin-chitosan A (0.04 part) was added to 36.75 parts of water, dissolved at room temperature, then 1 part of lamda-carrageenan was dissolved therein, the mixture was stirred with 42 parts of calcium secondary phosphate, 18 parts of glycerol, 1.2 parts of sodium laurylsulfate, 0.01 part of butyl p-hydroxy-benzoate and 1 part of peppermint fragrance, deaerated in vacuo and filled in a container to give tooth paste with good sweetness.

EXAMPLE 2.

Corn (80.45 parts), 12 parts of soybean cake, 5 parts of fish powder, 1.5 parts of calcium phosphate, 0.5 part of calcium carbonate, 0.5 part of salt and 0.05 part of dried thaumatin-chitosan A were mixed, the mixture was kneaded with 20 parts of 1% xanthan gum solution, granulated using a granulator and dried by heating to give granular feed for young pig with good sweetness.

Example 3.

Glacial acetic acid (0.04 part) was kneaded with 87.09 parts of water, 0.02 part of hydrolyzed chitosan B was dissolved therein at room temperature, then 0.03 part of thaumatin was similarly dissolved therein, the mixture was heated at 80° C. for 10 minutes after adding 0.4 part of sodium L-glutamate, 0.02 part of sodium 5'-inosinate, 1 part of lamda-carrageenan and 0.2 part of carotene dye, cooled down to 60° C., 1 part of salt, 10 parts of brewed vinegar and 0.2 part of spices were added and mixed for dissolving followed by cooling to give non-oil dressing with sweetness and good taste.

What is claimed is:

1. A method of preventing a decrease in sweetness of thaumatin, comprising adding at least one member selected from the group consisting of chitosan, hydrolyzed chitosan, and mixtures thereof to an aqueous solution containing thaumatin and a substance which decreases the sweetness of thaumatin, in an amount effective to prevent decrease in sweetness of thaumatin.

2. The method of claim 1 wherein said amount which is effective to prevent decrease in sweetness is 0.0002–100 parts by weight to 1 part by weight of thaumatin.

3. The method of claim 1 wherein thaumatin is in the form of an aqueous solution wherein said substance which decreases the sweetness of thaumatin is selected from the group consisting of coloring agents, polysaccharides, and mixtures thereof.

4. The method of claim 1 wherein the average molecular weight, as measured by gel permeation chromatography, of the hydrolyzed chitosan is about 2,000 to 100,000.

5. The method of claim 1 wherein chitosan is added to said aqueous solution.

6. The method of claim 1 wherein hydrolyzed chitosan is added to said aqueous solution.

7. The method of claim 1 wherein a mixture of chitosan and hydrolyzed chitosan is added to said aqueous solution.

8. The method of claim 5 wherein the amount of chitosan added is from about 0.0025 to about 1 part by weight of chitosan, to about 1 part by weight of thaumatin.

9. The method of claim 6 wherein the amount of hydrolyzed chitosan added is from about 0.0025 to about 10 parts by weight of hydrolyzed chitosan, to about 1 part by weight of thaumatin.

10. The method of claim 3 wherein said coloring agent is selected from the group consisting of Tartrazine, Sunset Yellow, Ponceau 4R, lac dyes and cochineal dyes of the anthraquinone series, red cabbage dyes of the anthocyanin series, annatto dyes of the carotenoid series, safflower yellow dyes of the flavonoid series, and mixtures thereof.

11. The method of claim 3 wherein said polysaccharide is selected from the group consisting of carrageenan, xanthan gum, sodium carboxymethylcellulose, sodium alginate, high methoxyl pectin, locust bean gum, guar gum, and mixtures thereof.

* * * * *